United States Patent [19]

Zhang et al.

[11] Patent Number: 5,800,412
[45] Date of Patent: Sep. 1, 1998

[54] HYDROPHILIC COATINGS WITH HYDRATING AGENTS

[75] Inventors: Xianping Zhang, Webster; Richard J. Whitbourne, Fairport, both of N.Y.

[73] Assignee: STS Biopolymers, Inc., Henrietta, N.Y.

[21] Appl. No.: 728,805

[22] Filed: Oct. 10, 1996

[51] Int. Cl.$^6$ ................................................ A61M 25/00
[52] U.S. Cl. .................... 604/280; 604/264; 604/283; 604/164; 604/165; 604/166; 604/167; 604/168; 604/169; 623/11; 428/35.7
[58] Field of Search ........................ 604/264, 283, 604/164–170, 265, 200; 623/11; 420/35.7

[56] References Cited

U.S. PATENT DOCUMENTS

| | | |
|---|---|---|
| 2,282,876 | 8/1981 | Flynn . |
| 3,661,634 | 5/1972 | Riley et al. . |
| 3,695,921 | 8/1968 | Sheppard et al. . |
| 3,861,396 | 1/1975 | Vaillancourt . |
| 3,939,049 | 2/1976 | Ratner et al. . |
| 4,055,682 | 10/1977 | Merrill . |
| 4,087,567 | 5/1978 | Sulllivan . |
| 4,100,309 | 7/1978 | Micklus et al. . |
| 4,112,925 | 9/1978 | Sullivan . |
| 4,127,647 | 11/1978 | Sato et al. . |
| 4,143,423 | 3/1979 | Sternlieb . |
| 4,169,163 | 9/1979 | Judd et al. . |
| 4,239,664 | 12/1980 | Teng et al. . |
| 4,373,009 | 2/1983 | Winn . |
| 4,381,008 | 4/1983 | Thomas et al. . |
| 4,442,133 | 4/1984 | Greco et al. . |
| 4,459,317 | 7/1984 | Lambert . |
| 4,473,670 | 9/1984 | Kessidis . |
| 4,482,577 | 11/1984 | Goldstein et al. . |
| 4,534,363 | 8/1985 | Gold . |
| 4,557,724 | 12/1985 | Gregonis et al. . |
| 4,585,666 | 4/1986 | Lambert . |
| 4,589,873 | 5/1986 | Schwartz et al. . |
| 4,642,267 | 2/1997 | Creasy et al. . |
| 4,678,660 | 7/1987 | McGary . |
| 4,682,607 | 7/1987 | Vaillancourt et al. . |
| 4,729,914 | 3/1988 | Kliment et al. . |
| 4,758,475 | 7/1988 | Eckes et al. . |
| 4,769,013 | 9/1988 | Lorenz et al. . |
| 4,781,703 | 11/1988 | Walker et al. . |
| 4,835,003 | 5/1989 | Becker et al. . |
| 4,872,867 | 10/1989 | Joh . |
| 4,876,126 | 10/1989 | Takemura et al. . |
| 4,879,135 | 11/1989 | Greco et al. . |
| 4,883,699 | 11/1989 | Aniuk et al. . |
| 4,906,237 | 3/1990 | Johansson et al. . |
| 4,977,901 | 12/1990 | Ofstead . |
| 4,990,357 | 2/1991 | Karakelle et al. . |
| 5,013,717 | 5/1991 | Solomon et al. . |
| 5,041,100 | 8/1991 | Rowland et al. . |
| 5,061,254 | 10/1991 | Karakelle et al. . |
| 5,061,738 | 10/1991 | Solomon et al. . |
| 5,084,315 | 1/1992 | Karimi et al. . |
| 5,129,890 | 7/1992 | Bates et al. . |
| 5,160,790 | 11/1992 | Elton . |
| 5,331,027 | 7/1994 | Whitbourne . |
| 5,416,131 | 5/1995 | Wolff et al. . |
| 5,452,726 | 9/1995 | Burmeister et al. . |
| 5,523,095 | 6/1996 | Wilson et al. . |
| 5,525,348 | 6/1996 | Whitbourne et al. . |

FOREIGN PATENT DOCUMENTS

| | | |
|---|---|---|
| 0 217 771 | 4/1987 | European Pat. Off. . |
| 0 328 421 | 8/1989 | European Pat. Off. . |
| 0371636 | 6/1990 | European Pat. Off. . |
| 0380102 | 8/1990 | European Pat. Off. . |
| 0405823 | 1/1991 | European Pat. Off. . |
| 0 586 324 | 3/1994 | European Pat. Off. . |
| 0 591 091 | 4/1994 | European Pat. Off. . |
| 90/03768 | 4/1990 | WIPO . |
| 90/05162 | 5/1990 | WIPO . |
| 94/16747 | 8/1994 | WIPO . |

OTHER PUBLICATIONS

McGraw–Hill Encyclopedia of Science & Technology, 6th Edition, 18 Sur–Tyr, 1987, p. 7.

Concise Encyclopedia of Polymer Science and Engineering, Kroschwitz, ed. Wiley 1990, pp. 458–459.

Donald H. Lorenz, Ph.D. "The Use of Hydromer Coatings on Medical Devices", Medical Plastics Technology Seminar, Oct. 4, 1984, Ann Arbor, Michigan.

Daniel Klempner, "Interpenetrating Polymer Networks" Angew. Chem. Int. Ed. Engl. vol. 17, pp. 97–106 (1978).

*Primary Examiner*—Michael Buiz
*Assistant Examiner*—N. Kent Gring
*Attorney, Agent, or Firm*—Spencer & Frank

[57] ABSTRACT

According to the invention, hydrating agents in ultrafine form may be incorporated in an organic coating solution with a uniform distribution that does not change due to settling. In preferred embodiments, the coating solution comprises salt dissolved in an appropriate organic solvent blend. In another embodiment, the hydrating agent may be in the form of ultrafine particles dispersed in the polymer solution. The dispersion may be obtained by adding a stream of the aqueous hydrating agent solution to the organic polymer solution in a controlled fashion, or salt particles may be formed in the polymer solution by acid-base neutralization in solution. The coating solutions are storage stable. When applied to a medical device, the coating solution produces a homogenous coating with desirable performance characteristics. The coatings of the invention adhere to the substrate but not to moist tissue with which they are placed in contact. The coatings of the invention provide indwelling devices with long-lasting lubricity after the device is inserted in a body.

37 Claims, No Drawings

HYDROPHILIC COATINGS WITH HYDRATING AGENTS

BACKGROUND OF THE INVENTION

1. Field of the Invention

The present invention relates to lubricious hydrophilic coatings with low cellular adhesion, methods of preparing them, and coating liquids used to prepare them. The coatings provide a friction-reducing surface in wet condition, and comprise salts or other hydrating agents that reduce adhesion to tissues.

2. Background Information

Lubricious hydrophilic coatings for medical devices become slippery when dipped in water, so that they are much easier to insert into a body. U.S. Pat. No. 5,331,027 describes such coatings having a hydrophobic component, a hydrophilic component, and additional substances such as plasticizers and stabilizers. However, when a wetted hydrophilic surface contacts salt-containing tissue and media, such as blood vessels, the digestive system, or the urinary tract, the coating may become drier and less lubricious, adherent to the tissue, and hence painful, difficult, and traumatic to remove.

U.S. Pat. No. 4,906,237 describes adding osmolarity-increasing compounds to a hydrophilic coating on a substrate by coating the substrate, and then dipping the hydrophilic surface in an aqueous solution of the osmolarity-increasing agents, and evaporating the water. The osmolarity-increasing compounds were said to reduce water loss from the coating. Disadvantages of this approach include the fact that it takes a long time to apply and dry the salt constituent, and requires an extra coating step, which can contribute to coating defects. Further, precipitation or crystallization of the osmolarity-increasing agents from aqueous solution can not be controlled during evaporation of water. Because the osmolarity-increasing agents retain water in a hydrophilic coating, it is difficult to remove water completely from the coating even with a long drying process, and the coated article surface may be sticky and difficult to handle. During the lengthy drying process, the saturated aqueous osmolarity-increasing agent solution forms a rough surface, which can cause abrasion and trauma during insertion or removal.

WO 94/16747, the publication of PCT/DK94/0035, describes including urea in a hydrophilic coating at a concentration of 5–6% by weight. A higher percentage is said to cause a smarting sensation during introduction.

U.S. Pat. No. 5,416,131 describes incorporating crushed salt crystals or other osmolarity-increasing agents as a suspension in an organic solvent-based coating solution for a hydrophilic coating. Disadvantages of this method include the need to mill the salt component in a crushing or grinding step, and the inability to control the particle size within a narrow range. Salt particles had sizes up to 50 microns. The larger particles can settle to the bottom of the coating mixture which makes it difficult to obtain a uniform coating dispersion, and in turn to obtain a uniform coating. The non-uniform, crushed particles and heterogeneous dispersion result in a rough coated surface.

U.S. Pat. No. 5,525,348 describes incorporating pharmaceutical agents into a cellulose ester coating. The pharmaceutical agents include heparin-quaternary ammonium compounds, antibiotics, and other compounds soluble in organic solvents. The pharmaceutical compounds were resistant to removal from the coatings in physiological solutions. The pharmaceutical agents of the '348 patent provide pharmaceutical efficacy but do not offer enhanced lubricity when inserted into physiological tissue.

Creasy, U.S. Pat. No. 4,642,267, describes a blend of polyurethane and polyvinylpyrrolidone, and coatings produced from them, one of which was prepared from a solution containing 2% chlorohexidine acetate. Creasy does not suggest using a higher concentration of salts such as would be sufficient to reduce adhesion of the coating to tissue during prolonged contact, and there is no teaching of coating liquids, coating methods, or coated articles having such properties.

SUMMARY OF THE INVENTION

This invention is in the crowded and mature art of hydrophilic lubricious coatings for medical devices. The invention succeeds where previous efforts at providing uniform water-retaining lubricious coatings have failed. The invention solves previously unrecognized problems due to the presence of coarse salt crystals in lubricious coatings. The methods and compositions of the invention differ from the prior art in solubilizing a hydrating agent in an organic coating solution of hydrophilic polymer, or providing an ultrafine dispersion of hydrating agent. These modifications were not previously known or suggested. The coating methods of the invention omit elements employed in the prior art—an extra coating step, or preparing salt particles by milling before preparing the coating solutions—without loss of performance.

According to the invention, hydrating agents may be uniformly distributed in a coating liquid, preferably an organic solvent blend, comprising hydrating agent dissolved in an appropriate solvent/polymer blend, or hydrating agent in the form of ultrafine particles having a particle size less than about 10 microns dispersed in the solvent/polymer blend. A dispersion according to the invention may preferably be obtained by adding a stream of a hydrating agent solution to the solvent/polymer blend in a controlled fashion, or the hydrating agent particles may be formed in the solvent/polymer blend by acid-base neutralization in the solvent/polymer blend. The hydrating agents are incorporated in the coating liquid without crushing or grinding, which are tedious and corrosive to equipment, generate irregularly sized and shaped particles, and may introduce contamination into the coating solutions. No water is used, or a small amount is used to dissolve the hydrating agents, which ensures a considerable reduction of time required for the production process because the organic solvents are easy to evaporate from the coating.

The hydrating agent is applied with the hydrophilic coating liquid without increasing the coating steps. It may also be incorporated in a hydrophobic base coat layer applied to the substrate.

When applied to a medical device, the coating solution produces a homogenous coating with desirable performance characteristics. The coated surfaces of this invention are smoother than the prior art because the hydrating agent is either in uniformly sized ultrafine particles or in solution, and is especially compatible with the polymers of the coating. This smoothness ensures physiologically acceptable low levels of trauma during insertion and removal of the coatings. The coatings of the invention adhere to the substrate but not to moist living tissue with which they are placed in contact, such as a urethra or blood vessel wall. The coatings of the invention provide indwelling devices with long-lasting lubricity after the device is inserted in physiological media.

A coating composition according to the invention comprises a hydrophilic polymer, a hydrophobic polymer, and a hydrating agent in an amount greater than about 5% selected from the group consisting of dissolved hydrating agent and an ultrafine dispersion of hydrating agent having particle size less than about 10 microns, the coating composition being adapted to adhere to a substrate as a homogeneous coating that becomes hydrated and lubricious when wet, and has physiologically acceptably low adhesion to physiological tissue after prolonged contact with the tissue. The prolonged period is predetermined by the person supervising the use of the coated device, such as a doctor, patient, or veterinarian. For example, the period may be that of a urinary catheterization, angioplasty, or otherwise. Typical indwelling times are in the range of a few minutes, but may be as long as an hour, a day, or more.

The hydrophilic polymer may be polyvinylpyrrolidone, polyethylene glycol, polyethylene oxide, polyvinyl alcohol, a polyether, polysaccharide, hydrophilic polyurethane, polyhydroxyacrylate, polymethacrylate, dextran, xanthan, hydroxypropyl cellulose, methyl cellulose; or a homopolymer or copolymer of a vinyl compound having polar pendant groups, N-vinyllactam such as N-vinylpyrrolidone, N-vinyl butyrolactam, N-vinyl caprolactam, an acrylate or methacrylate having hydrophilic esterifying groups, hydroxyacrylate, and acrylic acid; or a combination.

The hydrophobic polymer may be a cellulose ester or ether, ethyl cellulose, hydroxyethyl cellulose, cellulose nitrate, cellulose acetate, cellulose acetate butyrate, cellulose acetate propionate, polyurethane, polyacrylates, a natural or synthetic elastomer, rubber that is soluble in organic solvents, acetal, nylon, polyester, styrene polybutadiene, acrylic resin, polyvinylidene chloride, polycarbonate, homo and copolymers of vinyl compounds, polyvinylchloride, polyvinylchloride acetate, and combinations thereof.

The hydrating agent may be an inorganic salt or an organic salt, for example sodium chloride, calcium chloride, potassium chloride, potassium iodide, potassium nitrate, amines, sodium citrate, sodium acetate, ammonium acetate, or sodium benzoate, and combinations thereof. Preferably, the hydrating agent is an inorganic salt, the hydrophilic polymer is polyvinylpyrrolidone, and the hydrophobic polymer is selected from the group consisting of a cellulose ester and polyurethane.

The coating composition may form a layer applied to at least a portion of a substrate, or it may form an outer layer and an inner layer on the substrate, the outer layer comprising a hydrophilic polymer, and a hydrating agent in an amount greater than about 5% selected from the group consisting of dissolved hydrating agent and an ultrafine hydrating agent dispersion having particle size less than about 10 microns; and the inner layer comprising a hydrophobic polymer.

A preferred coating composition according to the invention has a hydrating agent at a concentration of from about 10% to about 30%, the hydrophilic polymer at a concentration of from about 25% to about 95%, and a hydrophobic polymer at a concentration of from about 0% to about 75%. Preferably, the hydrating agent has a concentration of from about 15% to about 25%, and the hydrophilic polymer has a concentration of from about 50% to about 85%.

In a two layer coating, the outer layer may preferably further comprise a hydrophobic polymer in a concentration up to about 70%, preferably between about 0% and about 5%, and the inner layer may further comprise a hydrophilic polymer in a concentration up to about 80%. The hydrating agent may have a concentration of about 20%, and the hydrophilic polymer a concentration of from about 75% to about 85%.

A coating liquid according to the invention comprises the coating composition in a single phase solvent liquid adapted to dissolve or to disperse the hydrating agent, comprising an organic solvent and water in an amount up to about 25% by volume, wherein the hydrophilic polymer is dissolved in the solvent and the hydrating agent is in a form selected from the group consisting of hydrating agent dissolved in the solvent liquid, and hydrating agent dispersed in the solvent liquid as an ultrafine dispersion having particle size less than about 10 microns. Preferably, the concentration of hydrophilic polymer is from about 5% to about 10% w/v, the concentration of hydrophobic polymer is less than about 0.1%, the concentration of water is less than about 10%, and the concentration of the hydrating agent is between about 0.1% and about 2.5%. Most preferably, the organic solvent comprises a polar solvent in which the hydrating agent is dissolved.

The organic solvent is preferably selected from ketones, esters, toluene, lactones, dimethylformamide, halogenated solvents, tetrahydrofuran, dioxane, amines, glycol butyl ether, alkyl acetates, acetonitrile, butyrolactone, ethyl acetate, acetone, chloroform, methylethylketone, methylene chloride, ethylene chloride, methanol, ethanol, propanol, and mixtures thereof. Most preferably, the hydrophilic polymer comprises polyvinylpyrrolidone, the hydrating agent is an inorganic salt, and the solvent blend comprises about 11% to about 20% butyrolactone, about 50% to about 80% aliphatic alcohol, about 18% to about 30% acetone, up to about 25% ethylene glycol or propylene glycol, up to about 20% N-methylpyrrolidone, up to about 20% dimethylsulfoxide, up to about 15% glycerol, and up to about 15% water.

The invention relates to a coating kit comprising at least one coating liquid comprising a single phase solvent liquid adapted to dissolve or to disperse a hydrating agent, comprising an organic solvent and water in an amount up to about 25% by volume, wherein the hydrophilic polymer is dissolved in the solvent and the hydrating agent is in a form selected from the group consisting of hydrating agent dissolved in the solvent liquid, and hydrating agent dispersed in the solvent liquid as an ultrafine dispersion having particle size less than about 10 microns. The coating kit may have a concentration of water up to about 10%. For a multi-layer application, the kit may further comprise a second coating liquid, used as a base coat, comprising a hydrophobic polymer dissolved in an organic solvent.

A method of coating a substrate according to the invention comprises:

providing a polymer solution comprising a single phase organic solvent blend adapted to dissolve or to disperse a hydrating agent, and a hydrophilic polymer dissolved in the solvent, adding to the organic solvent a hydrating agent in an amount of from about 0.3% to about 5% weight/volume, to produce a coating liquid selected from the group consisting of a hydrating agent solution and an ultrafine hydrating agent dispersion having particle size less than about 10 microns;

applying the coating liquid to the substrate;

evaporating the solvents to produce a homogeneous coating that adheres to the substrate, is lubricious when wet, and is non-adherent to physiological tissue after prolonged contact.

Preferably, the hydrophilic polymer has a concentration from about 0.5% to about 50% weight/volume, and the organic solvent blend comprises water in a single phase with the organic solvent in an amount up to about 25% by volume, and the method further comprises the step of applying to the substrate a base coat comprising a hydrophobic polymer.

The step of adding the hydrating agent may comprise dissolving the hydrating agent directly in the polymer solution. In a second alternative embodiment, the step of adding the hydrating agent comprises dissolving the hydrating agent in a solvent for the hydrating agent, to produce a hydrating agent solution, then adding the hydrating agent solution streamwise into the organic solvent blend to produce an ultrafine dispersion of hydrating agent particles. The solvent for the hydrating agent preferably comprises water. In a third embodiment, the step of adding the hydrating agent comprises adding an acid to the organic solvent blend, then adding a base to form a precipitate of hydrating agent in the form of an ultrafine dispersion.

The step of applying the coating liquid may comprise dipping the substrate in the liquid and removing the substrate from the liquid.

The invention also relates to a biomedical device produced by the process of the invention.

An article according to the invention comprises a substrate and a hydrophilic coating comprising:

a hydrophilic polymer, a hydrophobic polymer, and a hydrating agent in an amount of at least about 5% weight/volume, selected from the group consisting of dissolved hydrating agent and an ultrafine hydrating agent dispersion having particle size less than about 10 microns, the article having acceptable lubriciousness when inserted in living tissue, and causing no unacceptable trauma when removed from living tissue.

The hydrophilic polymer may preferably have a concentration of from about 25% to about 95% weight/volume; the hydrophobic polymer a concentration of from 0.1% to about 75% weight/volume, and the hydrating agent a concentration of from about 5% to about 50% weight/volume.

The substrate may preferably be selected from polyurethane, polyvinylchloride, other vinyl polymers, polycarbonate, polystyrene, nylon, polyesters and polyacrylates, polypropylene, polybutylene, teflon, polyvinylacetal, elastomers, latex) rubber, rubber, silicone, metal, glass, other plastic, and composites. It may be selected from catheters, guide wires, needles, wound drains, pacemaker leads, condoms, contact lenses, peristaltic pump chambers, arteriovenous shunts, gastroenteric feed tubes, endotracheal tubes, and implants.

Further aspects, objectives, and advantages will become apparent from a consideration of the following description.

DETAILED DESCRIPTION OF THE PREFERRED EMBODIMENTS

In describing preferred embodiments of the present invention, specific terminology is employed for the sake of clarity. However, the invention is not intended to be limited to the specific terminology so selected, and it is to be understood that each specific element includes all technical equivalents which operate in a similar manner to accomplish a similar purpose.

A coating according to the invention may have a single layer (a mono-coat) or two or more layers (a multi-coat), such as a hydrophobic base coat and a hydrophilic top coat. In a multi-coat embodiment, the base coat coating solution may include hydrophobic binding polymers alone or in combination. The hydrophobic polymer ensures adhesion of the hydrophilic lubricious coating on the substrate. Hydrophobic polymers may be included in a mono-coat, or in the base coat of a multi-coat coating. Also, including hydrophobic polymers in the top coat (hydrophilic layer) of a multi-coat coating can modify the degree of lubricity of the coating and improve the adhesion of the hydrophilic coating to the hydrophobic layer.

The single coating solution in a mono-coat embodiment, or the coating solution for the top, hydrophilic layer of a multi-coat embodiment, includes hydrating agents in suspension with particle size up to about 10 microns, or as a solution, in organic solvents with appropriate polymers. The organic solvents are easily removed to provide a dry, non-sticky, smooth coated surface. The top coat contains a hydrophilic polymer and a hydrating agent. To incorporate a hydrating agent such as NaCl into the top coat solution in the dissolved form, one employs solvents in which the hydrating agent has acceptable solubility. Water (up to about 10% or more of the total amount of solvents) can be used to help dissolve the hydrating agent. Alternatively, the hydrating agent is in an ultrafine dispersion.

A coating according to the invention is smooth to the touch when wet or dry, is lubricious (slippery) when wet so as to reduce friction, is adherent to the substrate after repeated abrasion, retains lubricity and remains hydrated during contact with physiological tissue, and does not cause problematic adherence of cells with which it is in contact. The coated surface thus reduces trauma during insertion and removal of a coated device to a medically acceptable low level. Coatings without the claimed combination of components have undesirable performance characteristics such as post-insertion adhesion to tissue, trauma, and loss of lubriciousness beyond what is physiologically acceptable, as distinct from coatings of the invention.

The coatings can be applied to any medical device to reduce friction in wet conditions. For example, the coatings may be applied to catheters, guide wires, needles, wound drains, pacemaker leads, condoms, contact lenses, peristaltic pump chambers, arteriovenous shunts, gastroenteric feed tubes and endotracheal tubes, or other implants of metal or polymer substrates. The substrates to which the coatings of the invention may be applied include any surface, preferably non-porous, such as polyurethane, polyvinylchloride, other vinyl polymers, polycarbonate, polystyrene, nylon, polyesters and polyacrylates, polypropylene, polybutylene, teflon, polyvinylacetal, natural or synthetic elastomer such as latex rubber or other rubber, silicone, metal, glass, other plastic, or a composite. Some substrates may require pretreatment or an undercoat to assure adequate adhesion of the hydrophilic coating.

Coated medical devices may be inserted into various types of living tissue and media containing physiological fluid. For example, such tissues include mucosa such as a urethra, a blood vessel, the heart, kidney, lungs, or other organs, the throat, the eye, or a joint.

The invention provides medical devices with a surface that is lubricious when wet, so that it is easy to insert into a bodily tissue or cavity, and remains hydrated and lubricious after contacting tissue such as mucosa for an extended period, so that the article can be easily removed after remaining in the body.

The coating liquids of the invention may be referred to as ultrafine hydrating agent blends (where ultrafine means that at least about 90% of the particles have less than about 10 micron diameter). Such a coating liquid may be a complete solution, that is a mixture uniformly dispersed throughout the liquid phase with homogeneity at the molecular or ionic level, or it may be a mixture of a polymer solution and insoluble hydrating agent particles dispersed as a suspension.

The coatings of the invention are also referred to as ultrafine hydrating agent blends, defined as a mixture so combined as to render the components indistinguishable from each other. Such a coating is a complex structure that may have one or a combination of several physical forms. It is a coating, defined as a material that forms a thin continuous layer over the substrate, and could be referred to as a film. It may be a solid mixture of the hydrophobic and hydrophilic polymers, ultrafine hydrating agent particles, additives, and solvent residues blended together. Alternatively, the coating may be a complete solid solution, that is a mixture uniformly dispersed throughout the solid phase with homogeneity at the molecular or ionic level, or it may be a combination of dissolved and mixed components, such as a mixture of a polymer coating solution and insoluble ultrafine hydrating agent particles in suspension. The coating may take the form of a composite, that is a structure composed of a mixture or combination of polymer and hydrating agent constituents that differ in form and chemical composition and are essentially insoluble in each other. It may be referred to as a matrix of polymer in which hydrating agent and other constituents are dispersed. The coating may comprise separate layers, discrete or intermingled, each of which may have any or several of these forms.

Thus, the structure of the coating is intermingled molecules of the polymer components and hydrating agent, in a homogeneous distribution with attributes of a solid phase mixture and solution. During drying, the polymers presumably become tangled together and obtain the desired characteristics of a hydrogel. The polymers of the hydrogel coatings of the invention may be chemically reacted together, such as an interpolymer of polyurethane and polyvinyl pyrrolidone, or they may be essentially unreacted co-deposited blends of hydrophilic and hydrophobic polymers with desired characteristics of hydrophilicity and durability. In either case, the hydrating agent is homogeneously and evenly dispersed.

The hydrophobic polymer according to the invention is non-toxic and physiologically acceptable. It dissolves in organic solvents, has a poor affinity for water, produces a water-insoluble coating film when applied to a substrate with the other coating components, and adheres to the substrate or a pre-coated substrate under applications involving insertion into tissue and removal. A hydrophobic polymer will generally absorb less than about 30%, preferably less than about 10% of its weight in water. The amount and kind of hydrophobic polymer must also be adapted to maintain coating integrity during swelling of the coating due to hydration of the hydrophilic polymer.

The hydrophobic component of coatings according to the invention can be any polymer presently known or later discovered having such characteristics. One group of hydrophobic polymers that is particularly suitable is the cellulose esters and ethers, and non-ether cellulose esters, such as ethyl cellulose, hydroxyethyl cellulose, cellulose nitrate, cellulose acetate, cellulose acetate butyrate, and cellulose acetate propionate. The cellulose esters are preferred. Other types of suitable polymers include polyurethane, polyacrylates, silicone, natural and synthetic elastomers, rubbers that are soluble in organic solvents, acetals, nylon, polyester, styrene polybutadiene, acrylic, polyvinylidene chloride, polycarbonate, polyimides, homo and copolymers of vinyl compounds, such as polyvinylchloride, and polyvinylchloride acetate. These polymers may be present alone or in combination. In multi-layer coatings, they may be in the base coat and/or the top coat layer. The final concentration of the hydrophobic polymer in the coating may be in any range known to persons of skill in the art or appropriate for the coatings of the invention.

A plasticizer such as camphor or dibutylphthalate may be included with the hydrophobic polymer in the coating or one of its layers to increase plasticity and improve the characteristics of the resulting coating.

A coating solution containing these hydrophobic polymers should include solvents capable of dissolving them and evaporating quickly and thoroughly. Examples of suitable solvents are ketones, esters, toluene, lactones, dimethylformamide, halogenated solvents, tetrahydrofuran, dioxane, amines, glycol butyl ether, alkyl acetates, acetonitrile, butyrolactone, ethyl acetate, acetone, chloroform, methylethylketone, methylene chloride, ethylene chloride, methanol, ethanol, propanol, and mixtures thereof. In a mono-coat embodiment, these solvents may be combined with solvents for the hydrophilic polymer and hydrating agent. In a multi-layer coating embodiment, in which a hydrophobic base coat is applied, the solvent system may be more particularly adapted to promoting adhesion than in a mono-coat in which all the polymers are applied together from one coating liquid. For example, an aggressive coating solution includes solvents that attack, soften, and swell the substrate and may promote adhesion of the hydrophobic polymer and the substrate.

The hydrophilic component is non-toxic and physiologically acceptable. It dissolves in organic solvents, and is partially or totally soluble in water. It absorbs and retains water and swells when wet in conjunction with the other coating components, absorbing at least its own weight in water, preferably more than about five times its weight, most preferably more than about ten times its weight, to produce a hydrogel that is suitably lubricious when wet. The amount and kind of hydrophilic polymer may readily be selected in conjunction with the hydrophobic polymer and hydrating agent to satisfy these criteria. Such hydrophilic polymers are well-known in the art, and a person of ordinary skill can readily find appropriate hydrophilic polymers that are compatible with the hydrophobic component, in the sense that together they form a hydrogel.

The hydrophilic component may be of any of the classes discussed in *Concise Encyclopedia of Polymer Science and Engineering*, Kroschwitz, ed. (Wiley 1990), pp. 458–59, which is incorporated herein by reference. Polymers such as polyvinylpyrrolidone, polyethylene glycol, polyethylene oxide, or polyvinyl alcohol are acceptable, alone or in combination. Examples of suitable hydrophilic polymers include homopolymers or copolymers of the following compounds: polyolefins such as vinyl polymers having polar pendant groups, N-vinylpyrrolidone, N-vinyllactam, N-vinyl butyrolactam, N-vinyl caprolactam, sodium styren sulfonate monomer, 2-acrylamido-2-methylpropane sulfonic acid, sodium vinyl sulfonate, vinyl pyridine, acrylates or methacrylates having hydrophilic esterifying groups. Other hydrophilic polymers include polyethers, polyethylene glycol, polysaccharides, hydrophilic polyurethanes, polyhydroxyacrylates, polymethacrylates, and copolymers of vinyl compounds and hydroxyacrylates or acrylic acid. Other examples include dextran, xanthan, hydroxypropyl cellulose, methyl cellulose, polyacrylamide, and polypeptides. Other hydrophilic components are known to persons of skill in the art. The concentration and type of this component in the coating is sufficient to absorb water and become lubricious when wet, while being compatible with the hydrophobic polymer component and retaining the hydrating agent in a homogenous distribution. The concentration is preferably between about 10% and about 98%, most preferably between about 70% and about 90%. In a multi-layer coating, where the hydrophilic component is present as a top coat, the top coat may also optionally include up to about 10% or more of a hydrophobic polymer. Some hydrophilic polymers are less hydrophilic, and contribute some of the binding characteristics defined above for a hydrophobic polymer, and some hydrophobic polymers have higher absorbancy of water, so that greater or lesser amounts of the particular components may be desirable to achieve the objects of the invention.

The hydrating agent may be any non-toxic, physiologically acceptable molecule that is compatible with the hydrophobic and hydrophilic polymers and inhibits the loss of lubriciousness and increased adhesion of a coating after extended exposure to a physiological medium. Presumably such adhesion to tissue and loss of lubriciousness derive at least in part from a tendency of the water in the hydrogel to migrate to the physiologic medium, and a resulting dehydration of the hydrogel. The hydrating agent perhaps increases osmolarity or otherwise maintains hydration. Without regard to the mechanism of action, it can be demonstrated that the hydrating agent reduces the adhesion of the coating to living tissue and reduces loss of lubriciousness. In coatings and methods according to the invention, the hydrating agent is compatible with the hydrogel coating and reduces adhesion without reducing the other desirable properties of the hydrogel.

Preferably the hydrating agent is a water-soluble, low molecular weight compound, for example with a molecular weight below 1000, more preferably below about 500, most preferably below about 100. Preferably the hydrating agent dissociates in aqueous environment such as would be found in living tissue. The hydrating agent is preferably an inorganic or organic salt. However, for purposes of this invention other molecules known to one of skill in the art may be used as well, so long as they have the requisite characteristics.

Examples of the hydrating agent thus include water-soluble inorganic salts and organic salts such as sodium chloride, calcium chloride, potassium chloride, potassium iodide, potassium nitrate, amines, sodium citrate, sodium acetate, ammonium acetate, dioctyl sodium sulfosuccinate, and sodium benzoate. Other examples include mono- and disaccharides, and sugar alcohols, such as glucose and sorbitol, and electrolytes. The inorganic salts are preferred. The various hydrating agents may be used alone or in combination in the hydrophilic coating. The concentration of hydrating agent in the hydrophilic coating may be any suitable amount, preferably between about 10% and about 50%, more preferably between about 20% and about 30%. In the coating liquid (a solution or suspension), the concentration of the hydrating agent may preferably be from about 0.2% to about 10%.

An ultrafine dispersion of hydrating agent according to the invention may be obtained by adding an aqueous hydrating agent solution to an organic polymer solution under controlled conditions to produce the desired particle size range and distribution. To determine the appropriate conditions for obtaining an ultrafine hydrating agent dispersion according to the invention, the following approach may be employed. Particle size may be controlled by the concentration of hydrating agent in the aqueous solution, the volume and rate of addition (whether poured in quickly or slowly, or added dropwise), and the rate of stirring. The resulting particle size can be measured by placing a droplet of the suspension on a glass slide under a microscope. The optimal conditions are selected as those providing the desired particle size range and distribution. A suitable suspension has particle size less than about 10 microns, meaning that less than about 10% of the particles were larger than 10 microns, and most of the particles fall in the size range of about 5 to about 10 microns.

Alternatively, the hydrating agent may be, dissolved in a non-aqueous solvent for the hydrating agent, such as an ethylene glycol, and then added to a polymer solvent system in which the hydrating agent precipitates as ultrafine particles.

Lubricious additives such as surfactants, waxes, lubricants, soap, and detergents may also be added as desired. The lubricious additives may not contribute much osmolarity to the coating but can increase lubricity when wet, and reduce adhesion, and their low solubility in water helps them remain in the coating. Other additives may include alcohols, acids, resins, waxes, fibers, pigments, dyes, and fragrances.

The hydrophilic polymers of the coating may be applied as a liquid comprising any combination of organic solvents that are readily evaporated during the drying and curing process. In a mono-coat embodiment, the same solvent system is used for both the hydrophilic and hydrophobic components. In a multi-coat embodiment, the hydrophilic coating liquid may include the same solvents as the hydrophobic polymer solvent listed above, or a variation adapted to incorporate the hydrating agent and confer other desirable features of the coating.

For example, for dissolved hydrating agent coatings, the solvents must be able to dissolve the hydrating agent. Minor amounts of water may be added provided the blend does not separate into a two phase system. A polar solvent like ethanol helps maintain a one phase system containing water. Diols and triols may be used to dissolve sodium chloride, preferably ethylene glycol and propylene glycol.

As described in the examples, some solvent blends that were found to be suitable to dissolve and blend the various coating components in a homogeneous formulation include butyrolactone/ethanol, ethylene glycol/N-methyl-2-pyrrolidone(NMP)/ethanol, ethylene glycol/DMSO/ethanol, and water/glycerol/butyrolactone/ethanol. With PVP as a hydrophilic polymer, a suitable solvent blend may include about 11% to about 20% butyrolactone, about 50% to about 80% aliphatic alcohol such as ethanol or isopropanol, about 18% to about 30% acetone, about 25% ethylene glycol or propylene glycol, about 13% to about 20% NMP, about 20% DMSO, about 15% glycerol, and up to about 15% water. Many other solvent blends will be suitable.

The hydrating agent is uniformly and homogeneously distributed as part of the coating blend. With ultrafine hydrating agent particles smaller than about 10 microns, the coating is quite homogenous and is observed to be smooth to the eye and to the touch. With dissolved hydrating agent, it is expected that there is homogeneity down to the molecular level. A coating according to the invention is homogeneous as to the hydrating agent, but also in that the polymer component is uniformly distributed throughout the coating.

A coating according to the invention is clear if all components are dissolved and milky or cloudy if the hydrating agent is in an ultrafine dispersion. Coloring agents may be added if desired for esthetic or quality control purposes.

In a method of producing a mono-coat embodiment according to the invention, there is only one coating step in which hydrophobic polymer, hydrophilic polymer, and hydrating agents are applied simultaneously. The substrate is dipped in the hydrophobic coating liquid, then withdrawn and dried, preferably at elevated temperature, to speed the process of drying and curing. To obtain an even coating, the substrate may preferably be removed at a rate such that the liquid flows back into the reservoir at the rate of removal, to minimize sag. The rate of removal should be slow enough relative to the rate of flow that a uniform coating thickness is formed. These rates depend on the viscosity, temperature, and wetting of the substrate. The coating solutions are typically thicker than water, but not as thick as a syrup. The coating may be sprayed, brushed, poured, or pumped onto the substrate, or any other appropriate method of application may be used.

In a multi-coat method according to the invention, a substrate is first coated with a hydrophobic layer, after a precoat step, if appropriate. The coating process for the hydrophobic layer is as set forth above. The coating process is then repeated with the hydrophilic coating liquid.

The transparent coating solutions and ultrafine dispersions according to the invention provide a process benefit in that there is no need to agitate the coating liquid to assure uniform and reproducible coatings. Below about 10 microns, particles tend not to settle quickly enough to require continuous agitation. Thus, the coating solutions of the invention are storage stable for at least one day and do not require mixing during coating, although they may require mixing or shaking after prolonged storage (more than a day for dispersions, at least weeks for solutions), prior to coating.

In the top layer of a two layer coating, the ratio of PVP to hydrophobic polymer may be over 100:1. In a one coat process, the coating solution may contain a higher percentage of the hydrophobic polymer.

For plastic tubing used in urethral applications, a multi-coat is preferred. The base coat may preferably include nitrocellulose, dibutylphthalate, camphor, and polyvinylbutyral applied from a blend of organic solvents. A preferred top coat is applied using a coating solution containing NaCl 19%, polyvinylpyrrolidone (PVP) 79.1%, and urea 1.9% (weight percent of solids), dissolved in an organic solvent mixture of propylene glycol 27.5%, ethanol 51.5%, 4-butyrolactone 11%, and water 10% (volume percent of liquids). The top coat coating liquid is a clear solution that looks the same as an equivalent top coat solution without hydrating agent. Optical clarity indicates complete solution.

Two-layer multi-coat coatings according to the invention were smoother when dry than the salt-containing catheter coating sold by Astra AB under the trade name LoFric, and coatings of the invention have lower cellular adhesion when placid in contact with living physiological fluid-containing tissue. Coatings of the invention are very slippery and smooth when wet. A test of lubriciousness in the urethras of male rabbits showed that the new coating has friction of about one fifth as compared to conventional coatings without hydrating agent.

Examples of finished coatings according to the invention may have concentrations and other parameters as in the following paragraphs, although in some embodiments other concentrations and parameters may be appropriate to achieve the benefits of the invention, depending on the polymer system, the solvents, the hydrating agent, the substrate, the application, and other variables. Accordingly, the concentration of hydrating agent in the coating may be in the range of about 5% to about 50%, preferably from about 10% to about 30%, most preferably about 20% (concentrations given as weight %). Exemplary concentrations of hydrophilic polymers may be from about 20% to about 98%, preferably over about 50%. The concentration of hydrophobic polymer may be from 0% up to about 80%, preferably less than about 20%, for example about 5% with many polymers. The thickness of the coating may be about 5 to about 15 microns or thicker, preferably about 7 to about 9 microns.

A multi-layered coating according to the invention may have a hydrophobic base coat having a concentration of hydrophobic polymer of about 20% to about 100%, preferably about 80% to about 90%. The concentration of the hydrophilic polymer in the base coat may be from 0% to about 80%, preferably less than about 20%, for example about 10%. Hydrating agent may also be included in the base coat.

The hydrophilic top layer of a multilayer coating may have a concentration of the hydrophilic polymer from about 30% to about 95%, preferably about 75% to about 95%, for example about 90%. The top coat may also include hydrophobic polymer in a concentration from 0% to about 70%, preferably about 15% to about 25%, for example about 5%. The hydrating agent concentration in the hydrophobic layer may be from about 2% up to about 50%, preferably about 10% to about 30%, for example about 20%.

EXAMPLES

In Examples 1–16, the following method was used to provide a hydrophobic coating (a base coat). A coating solution was prepared containing 5.4 g low viscosity ½ second nitrocellulose, 2.0 g dibutylphthalate, 1.5 g camphor and 1.9 g polyvinylbutyral, dissolved in a solvent mixture of 36 ml toluene, 13.1 ml butylacetate, 5.9 ml isopropanol, 25.4 ml ethylacetate, 18.1 ml ethanol and 1.5 ml acetone. 8.0 French plastic catheter tubing made of polyvinylchloride was dip coated in the above base coat solution and dried for 5 minutes at 65° C. The tubing with hydrophobic base coat was then dip coated with one of the following hydrophilic coatings to produce a hydrogel top coat. This type of base coat is acceptable for polyvinylchloride, polyurethane, and other substrates.

A top coat was then applied, as described below in examples 1–16, and the surface properties of the resulting coatings were evaluated by rabbit urethra test, histological test, and subjective tests.

Rabbit urethra test: Male Rabbits were weighed and anesthetized. The catheters were soaked in sterile water for 30 seconds and then inserted into the urethra of each rabbit until bladder drainage occurred. The catheters were removed at various time intervals by motor equipped with a force meter. The maximum force (in grams) required to pull the catheter out of the rabbit urethra was defined as the peak force. The smaller the peak force, the lower the friction of the catheter surface.

Histological test (cell counts): This test evaluates the adhesion of cells on the surface of a catheter after insertion into a rabbit urethra. After the catheters were pulled out of the rabbit urethra the portions that had been inserted were cut into pieces. Then the pieces were cast in paraffin and sliced in four sections each. The cells on each section were stained and counted.

Tactile and visual tests: The coated catheter was immersed in water and tested for lubricity and surface smoothness by rubbing with fingers. Coatings were observed for smoothness, clarity, and evenness.

Adhesion: The abrasion resistance of the coating was evaluated by rubbing the coated tubing 50 cycles with a wet paper towel. Retaining much of the initial lubricity after rubbing indicates good adhesion of the coating.

Table 1 shows the approximate percentage of components in the coating liquids and in the solid coating composition of the top (hydrophilic) layer.

Example 1

In Examples 1 to 7, a hydrophilic coating solution containing dissolved salt was prepared. The salts were combined with an appropriate blend of organic solvents and hydrophilic polymers to obtain a solution that is transparent, and stable at room temperature.

A coating solution was prepared as follows. Sodium chloride 1.2 g was dissolved in 25 ml of ethylene glycol, to which was added powdered polyvinylpyrrolidone (PVP) 5.4 g, nitrocellulose 0.05 g, 21 ml butyrolactone and 50 ml ethanol. This was shaken to provide a homogeneous solution. Polyvinylchloride tubing coated with a base coat as described above was coated with this solution and dried for 60 minutes at 70° C.

The coating was lubricious, but rough when wet. The coating had good abrasion resistance.

Example 2

A coating solution was prepared by a similar method as in Example 1. Sodium chloride 1.2 g was dissolved in 25 ml of ethylene glycol, to which was added powdered PVP 5.4 g, nitrocellulose 0.05 g, 21 ml N-methyl-2-pyrrolidone (NMP), and 50 ml ethanol. This produced a homogeneous solution. The coating was lubricious when wet and abrasion resistant.

Example 3

A coating solution was prepared as in the previous examples, containing sodium chloride 1.2 g dissolved in 25 ml of ethylene glycol, powdered PVP 5.4 g, nitrocellulose 0.05 g, 21 ml dimethyl sulfoxide, and 50 ml ethanol. This produced a homogeneous solution. The coating was lubricious when wet.

Example 4

A coating solution was prepared containing sodium chloride 1.2 g dissolved in 5 ml of water, powdered PVP 5.4 g, and 15 ml of glycerol, 20 ml butyrolactone, and 50 ml ethanol. This produced a homogeneous solution. The coating was lubricious and smooth when wet.

Example 5

A coating solution was prepared containing powdered PVP 5.4 g, dioctyl sodium sulfosuccinate 1.0 g, nitrocellulose 0.05 g, 15 ml butyrolactone, and 56 ml ethanol. This produced a homogeneous solution. The coating was lubricious when wet.

Example 6

A coating solution was prepared containing powdered PVP 7.6 g, ammonium acetate 1.0 g, 21 ml NMP and 78 ml ethanol. This is a homogeneous solution. The coating was lubricious and smooth when wet.

Example 7

A coating solution was prepared containing powdered PVP 6.1 g, calcium chloride 2.0 g, 15 ml butyrolactone and 70 ml ethanol. This produced a homogeneous solution. The coating was lubricious and smooth when wet but not as flexible as the previous examples. There did not seem to be much difference in coating quality in the range of 10% to 25% calcium chloride.

Example 8

In examples 8 to 11, a hydrophilic coating dispersion of salt in organic solvents was formed. Sodium chloride was dissolved in water close to the saturation point, to minimize the amount of water introduced, and was added streamwise into a solution of PVP in organic solvents under fast stirring at room temperature. Sodium chloride was precipitated as particles.

A coating solution was prepared containing powdered PVP 7.1 g, nitrocellulose 0.1 g, ethanol 78 ml, and acetone 18 ml. A stream of 25% NaCl in water (w/w) was added, totalling 5.0 ml. This produced a suspension with particle size generally in the range of 5 to 10 μm. The coating was lubricious and smooth when wet.

Example 9

A coating solution was prepared containing powdered PVP 5.4 g, ethanol 78 ml, and acetone 18 ml. A stream of 25% NaCl in water was added, totalling 5.0 ml. This produced a suspension with particle size generally in the range of 5 to 10 μm. The coating was lubricious and smooth when wet. The force required to pull out the catheter from a rabbit urethra was significantly reduced.

Example 10

A coating solution was prepared containing powdered PVP 5.4 g, nitrocellulose 0.1 g, ethanol 78 ml, and butyrolactone 18 ml. A stream of 25% NaCl in water was added, totalling 5.0 ml. This produced a suspension which separated to two layers after one hour. The suspension was stirred before applying the top coat. The coating was lubricious and smooth when wet.

Example 11

A coating solution was prepared containing powdered PVP 5.4 g, urea, 0.1 g, ethanol 51 ml, acetone 30 ml, and NMP 13 ml. A solution of NaCl 1.8 g in 5.5 ml water was added. The salt formed a suspension with particle size generally in the range of 5 to 10 μm. The coating was lubricious and smooth when wet.

Example 12

In this example, ultrafine salt particles were formed in situ in a blend of organic solvents. An aqueous solution of sodium acetate was added to a mixture of hydrochloric acid in a solution of PVP in organic solvents. Sodium chloride was formed as an ultrafine particle precipitate.

A coating solution was prepared containing powdered PVP 7.2 g, sodium acetate 2.0 g in 5 ml water, 37% commercial grade hydrochloric acid 0.2 ml, ethanol 67 ml, and butyrolactone 20 ml, to obtain a salt suspension. The coating was lubricious and smooth when wet.

Example 13

Examples 13 to 16 include salts in solution in the coating liquids. In this example, a coating solution was prepared containing powdered PVP .5.4 g, NaCl 1.3 g, urea 0.13 g, ethanol 50 ml, butyrolactone 11 ml, propylene glycol 24 ml, and water 10 ml. The coating was lubricious and smooth when wet. The rabbit test showed that the force required to remove the catheter from a rabbit urethra was significantly reduced. The coating was smoother when wet, and more slippery than those of Example 14 and Example 15.

Example 14

A coating solution was prepared containing powdered PVP 5.4g, NaCl 1.25 g, urea 0.1 g, ethanol 50 ml, NMP 21 ml, and ethylene glycol 25 ml. This produced a homogenous solution. The coating was lubricious when wet. The rabbit test showed that the force required to remove the catheter from a rabbit urethra was significantly reduced compared to a control, and there were fewer cells adhering to the coating according to the histological test.

Example 15

A coating solution was prepared containing powdered PVP 5.4 g, NaCl 1.3 g, urea 0.2 g, ammonium acetate 0.4 g, ethanol 50 ml, butyrolactone 20 ml, and ethylene glycol 25 ml. This produced a homogenous solution. The coating was lubricious when wet, and was smoother than the coating of Example 14. The rabbit test showed that the force required to remove the catheter from a rabbit urethra was significantly reduced, and there were fewer cells adhering from a rabbit urethra according to the histological test.

TABLE 1

Percentage of components in hydrophilic coatings

| | % (w/v) in liquid | | | weight % in solid | | |
|---|---|---|---|---|---|---|
| Examples | HA | PVP | CE | HA | PVP | CE |
| 1 | 1.25 | 5.6 | 0.05 | 18.05 | 81.2 | 0.75 |
| 2 | 1.25 | 5.6 | 0.05 | 18.05 | 81.2 | 0.75 |
| 3 | 1.25 | 5.6 | 0.05 | 18.05 | 81.2 | 0.75 |
| 4 | 1.33 | 6.0 | 0 | 18.2 | 81.8 | 0 |
| 5 | 1.4 | 7.6 | 0.07 | 15.5 | 83.7 | 0.8 |
| 6 | 1.0 | 7.7 | 0 | 11.6 | 88.4 | 0 |
| 7 | 2.4 | 7.2 | 0 | 24.7 | 75.3 | 0 |
| 8 | 1.24 | 7.0 | 0.1 | 14.8 | 84.0 | 1.2 |
| 9 | 1.24 | 5.3 | 0 | 18.8 | 81.2 | 0 |
| 10 | 1.3 | 5.6 | 0.1 | 18.5 | 80.0 | 1.5 |
| 11 | 1.92 | 5.7 | 0 | 25.1 | 74.9 | 0 |
| 13 | 1.47 | 5.68 | 0 | 20.9 | 79.1 | 0 |
| 14 | 1.31 | 5.6 | 0 | 19.0 | 81.0 | 0 |
| 15 | 2.0 | 6.3 | 0 | 24.1 | 75.9 | 0 |

HA = hydrating agent
PVP = polyvinylpyrrolidone
CE = cellulose ester

Example 16

This example describes the rabbit urethra test and histological evaluation, procedures which may be used to assess lubricious coatings of catheters and the ability to maintain lubricity after extended catheterization.

Test Article: 8.0 French polyvinyl chloride catheter tubing was coated with salt-containing coatings according to the Examples. As a control, 8.0 French catheter tubing was coated with the same base coat as in the Examples, and a top coat equivalent to the top coat in Examples 1–3, but without salt. This coating contains about 99% PVP and about 1% nitrocellulose.

Methods: Aseptic technique was used throughout the insertion procedure. Rabbits were weighed and then anesthetized. Harkness & Wagner, "The Biology of Rabbits and Rodents", Williams and Wilkins, Baltimore, 1995.

Catheter tubing was coated according to the examples. Salt free coatings were applied as controls. These had the same base coat as in the examples, and a top coat equivalent to the top coat in Examples 1–3, but without salt. Uncoated controls were also tested.

Each catheter was soaked in sterile water for 30 seconds and then inserted into the urethra of a rabbit until bladder drainage occurred. The time of placement was noted. At various time intervals the catheters were removed using a motor (Compumotor PDX13-67-61), equipped with a force meter (Chatillon DFIS2), that recorded the force in gram units. The peak force is the maximum reading from the force meter. The animals remained anesthetized throughout the procedure.

In addition, certain catheters were harvested for histological evaluation. This was performed by cutting three pieces of the catheter, approximately four cm in length each, from the portion that contacted the urethra. The length of contact, or depth of insertion, was generally about 15 cm, but varied between about 11 and 19 cm. The pieces were cast in paraffin. One slice of 5–10 μm was made of each piece and stained with Haematoxylin and Eosin to color the nucleus of any adherent cells blue and the cell membrane red, therefore enabling a cell count to be performed.

Results: Rabbit urethra test results are reported in Table 2.

TABLE 2

| NUMBER OF SAMPLES (n=) | COATING TYPE | INDWELLING TIME (min) | PEAK FORCE AVERAGE (g) |
|---|---|---|---|
| 1 | Uncoated Catheter | 5 | 10 |
| 1 | Uncoated Catheter | 60 | 50 |
| 10 | Non-Salt Coating | 5 | 78 |
| 10 | Non-Salt Coating | 60 | 118 |
| 2 | Example 14 | 5 | 18 |
| 2 | Example 14 | 60 | 20 |
| 2 | Example 15 | 5 | 28 |
| 2 | Example 15 | 60 | 23 |
| 2 | Example 7 | 5 | 33 |
| 2 | Example 7 | 60 | 40 |
| 4 | Example 13 | 5 | 12 |
| 2 | Example 13 | 60 | 21 |
| 2 | Example 9 | 2 | 27 |
| 2 | Example 9 | 60 | 15 |

Uncoated Nelaton catheters were tested, for comparison. These uncoated controls are non-lubricious and difficult to insert.

Control non-salt coatings are lubricious and relatively easy to insert, but after an insertion time of five minutes, the average peak force for removal was 78 g (n=10), with a range from 32 g to 126 g. With an insertion time of 60 minutes, the average peak force of removal rose to 118 (n=10), with a range from 30 g to 210 g. This data suggests that the coatings are adhering to the urethral tissue, even more than uncoated catheters.

Coatings according to the invention had significantly reduced friction as compared to uncoated controls and control coatings without salt. This advantage was true for coatings containing salt in solution (Examples 7 and 13–15) and for coatings containing an ultrafine dispersion of salt particles (Example 9). Data showing the advantage of coatings according to the invention was consistent with other observations, including anecdotal evidence from cathetherization volunteers.

Rabbit urethra friction tests were also conducted on a commercially available salt containing coating, the Astra LoFric coating. This coating had peak force of removal comparable to the data for coatings according to the invention. However, the LoFric coating was noticeably rough to the touch and had high cell counts caused presumably by abrasion and irritation of the rabbit urethra. Coatings of the invention are smooth to the touch and have lower cell counts.

Thus, coatings according to the invention retain sufficient lubriciousness that the peak force for removal from a rabbit urethra is generally less than about 35 g after five minutes, preferably less than about 20 g, and is generally less than about 45 grams after 60 minutes, preferably less than about 20 g.

Histological evaluation results are as follows. In general, the coatings of the invention had few or no red blood cells and low numbers of epithelial cells adhering to them after coated catheters were removed from a rabbit urethra.

Surfaces of particular coatings according to the invention and controls (Examples 13 and 14) were examined after catheters were removed from a rabbit urethra and rinsed. Indwelling time was 60 minutes, and indwelling length was about 15 cm. Coatings according to the invention had fewer than about 10 red blood cells and an average of fewer than about 50 epithelial cells adhering to them. Preferred coatings (examples 13 and 14) had no red blood cells and about 20 epithelial cells adhering. Conventional non-salt hydrogel coatings had no red blood cells and an average of 31 epithelial cells adhering to them (n=10). This reflects adhesion to the cells of urethral tissue, in addition to the high peak force (low lubriciousness) of such non-salt coatings after 60 minutes contact with the urethra. A conventional salt hydrogel coating (Astra LoFric catheter) had an average of 11 red blood cells and 53 epithelial cells adhering to them (more than the coatings of the invention) (n=10).

Higher numbers of epithelial cells adherent Lo the coatings reflect greater cellular adhesion, and are undersirable. High numbers of red blood cells reflect trauma and micro-hemmorhage of the tissue inside the urethra. Thus, the histological data shows that the coatings according to the invention had fewer adherent red blood cells and epithelial cells than the conventional salt-containing coatings, reflecting less adhesion to tissue during indwelling, and less trauma and microhemmorhage of the tissue inside the urethra during insertion and removal of the catheter. These performance advantages of the coating according to the invention derive from the composition of the coatings and augment the advantageous methods of making the coatings.

In summary, coatings according to the invention, when inserted into a rabbit urethra to the point of bladder drainage, removed after 60 minutes indwelling, and subjected to histological examination, as described herein, have less than about 10 adherent red blood cells, preferably less than about 5, and less than about 50 adherent epithelial cells, preferably less than about 25. Conventional coatings have greater amounts of adherent cells, and other disadvantages.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

We claim:

1. A method of coating a substrate comprising:

providing a hydrophilic polymer dissolved in a solvent, the hydrophilic polymer solvent adapted to dissolve or to disperse a hydrating agent, and comprising less than about 25% water by volume;

adding to the hydrophilic polymer solvent a hydrating agent in an amount greater than about 10% as a percentage of the total weight of the hydrophilic polymer and hydrating agent, the hydrating agent being dissolved or an ultrafine dispersion having particle size less than about 10 microns;

coating the substrate with the hydrophilic polymer and hydrating agent in the hydrophilic polymer solvent; and forming a hydrophilic coating that adheres to the substrate, becomes lubricious when wet, retains physiologically acceptable lubriciousness after contacting physiological media during a predetermined period of indwelling, is sufficiently smooth to avoid causing physiologically unacceptable trauma to tissue during insertion or removal, and has physiologically acceptable low cellular adhesiveness after contacting the tissue during a predetermined period of indwelling.

2. The method of claim 1, wherein the hydrating agent is a salt.

3. The method of claim 1, further comprising adding a hydrophobic polymer to the hydrophobic polymer solvent.

4. The method of claim 1, further comprising adding a hydrophobic polymer dissolved in a hydrophobic polymer solvent, applying the hydrophobic polymer to the substrate as a base coat, and at least partially evaporating the hydrophobic polymer solvent before applying the hydrophilic polymer and hydrating agent.

5. The method of claim 1, wherein the step of adding the hydrating agent comprises dissolving the hydrating agent directly in the hydrophilic polymer solution.

6. The method of claim 1, wherein the step of adding the hydrating agent comprises the steps of dissolving the hydrating agent in a hydrating agent solvent to produce a hydrating agent solution, then adding the hydrating agent solution steamwise into the hydrophilic polymer solution to produce an ultrafine dispersion of hydrating agent particles having particle size less than about 10 microns.

7. The method of claim 6, wherein the hydrating agent solvent comprises water.

8. The method of claim 1, wherein the step of adding the hydrating agent comprises, without regard to order, adding an acid to the polymer solution, and adding a base to the polymer solution, so that the acid and base neutralize each other and form an ultrafine dispersed precipitate of hydrating agent.

9. The method of claim 1, wherein the hydrophilic polymer has a concentration in the hydrophilic polymer solvent of from about 0.5% to about 50% weight/volume, and the concentration of the hydrating agent is at least about 20% by weight as a percentage of solids.

10. An article produced by the method of claim 1.

11. An article comprising a coated substrate, comprising:

a hydrophilic polymer;

a hydrophobic polymer; and at least about 10% by weight of a hydrating agent selected from the group consisting of dissolved hydrating agent and an ultrafine dispersion of the hydrating agent having particle size less than about 10 microns;

the components of the coating being mutually compatible when blended together, the coating composition forming a hydrophilic coating that adheres to the substrate, becomes lubricious when wet, retains physiologically acceptable lubriciousness after contacting physiological media during a predetermined period of indwelling, is sufficiently smooth to avoid causing physiologically unacceptable trauma to tissue during insertion or removal, and has physiologically acceptable low adhesiveness to tissue after contacting the tissue during a predetermined period of indwelling.

12. An article according to claim 11, wherein the hydrophilic polymer has a concentration of from about 25% to about 95% by weight of the coating, the hydrophobic polymer has a concentration of from 0.1% to about 75% by weight of the coating, and the hydrating agent is a salt.

13. An article according to claim 12, wherein the substrate is selected from the group consisting of polyurethane, polyvinylchloride, other vinyl polymers, polycarbonate, polystyrene, nylon, polyesters and polyacrylates, polypropylene, polybutylene, tetrafluoroethylene, polyvinylacetal, elastomers, latex rubber, rubber, silicone, other plastic, metal, glass, and composites.

14. An article according to claim 12, wherein the substrate is selected from the group consisting of catheters, guide wires, needles, wound drains, pacemaker leads, condoms, contact lenses, peristaltic pump chambers, arteriovenous shunts, gastroenteric feed tubes, endotracheal tubes, and implants.

15. A composition for coating a substrate, comprising:
a hydrophilic polymer;
a hydrophobic polymer; and
at least about 10% by weight of solids of an ultrafine hydrating agent selected from the group consisting of dissolved hydrating agent and an ultrafine dispersion of the hydrating agent having particle size less than about 10 microns;
the components of the composition being mutually compatible when blended together, the composition forming a hydrophilic coating that adheres to the substrate, becomes lubricious when wet, retains physiologically acceptable lubriciousness after contacting physiological media during a predetermined period of indwelling, is sufficiently smooth to avoid causing physiologically unacceptable trauma to tissue during insertion or removal, and has physiologically acceptable low cellular adhesiveness after contacting the tissue during a predetermined period of indwelling.

16. A composition according to claim 15, wherein the hydrating agent is a salt.

17. A composition according to claim 15, wherein the hydrophilic polymer is selected from the group consisting of polyvinylpyrrolidone, polyethylene glycol, polyethylene oxide, polyvinyl alcohol, polyether, polysaccharide, hydrophilic polyurethane, polyhydroxyacrylate, polymethacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof; and the hydrophobic polymer is selected from the group consisting of cellulose esters and ethers, ethyl cellulose, hydroxyethyl cellulose, cellulose nitrate, cellulose acetate, cellulose acetate butyrate, cellulose acetate propionate, polyurethane, polyacrylate, natural and synthetic elastomers, rubber, acetal, nylon, polyester, styrene polybutadiene, acrylic resin, polyvinylidene chloride, polycarbonate, homopolymers and copolymers of vinyl compounds, polyvinylchloride, polyvinylchloride acetate, and combinations thereof.

18. A composition according to claim 15, wherein the hydrating agent is an inorganic salt, the hydrophilic polymer is polyvinylpyrrolidone, and the hydrophobic polymer is selected from the group consisting of a cellulose ester and polyurethane.

19. A composition according to claim 15, further comprising a substrate, wherein the coating composition forms a film applied to at least a portion of the substrate.

20. A composition according to claim 19, wherein the coating has less than about 10 adherent red blood cells and less than about 50 adherent epithelial cells according to a rabbit urethra test.

21. A composition according to claim 20, wherein the film comprises an outer layer and an inner layer on the substrate, the outer layer comprising the hydrophilic polymer and the hydrating agent, and the inner layer comprising the hydrophobic polymer.

22. A composition according to claim 21, wherein the hydrophilic polymer is selected from the group consisting of polyvinylpyrrolidone, polyethylene glycol, polyethylene oxide, polyvinyl alcohol, polyether, polysaccharide, hydrophilic polyurethane, polyhydroxyacrylate, polymethacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof.

23. A composition according to claim 21, wherein the hydrophobic polymer is selected from the group consisting of cellulose esters and ethers, ethyl cellulose, hydroxyethyl cellulose, cellulose nitrate, cellulose acetate, cellulose acetate butyrate, cellulose acetate propionate, polyurethane, polyacrylate, natural and synthetic elastomers, rubber, acetal, nylon, polyester, styrene polybutadiene, acrylic resin, polyvinylidene chloride, polycarbonate, homopolymers and copolymers of vinyl compounds, polyvinylchloride, polyvinylchloride acetate, and combinations thereof.

24. A composition according to claim 21, wherein the hydrating agent is selected from the group consisting of inorganic salt, organic salt, sodium chloride, calcium chloride, potassium chloride, potassium iodide, potassium nitrate, amines, sodium citrate, sodium acetate, ammonium acetate, sodium benzoate, and combinations thereof.

25. A composition according to claim 21, wherein the outer layer further comprises a hydrophobic polymer in a concentration up to about 70%.

26. A composition according to claim 21, wherein the inner layer further comprises a hydrophilic polymer in a concentration up to about 80%.

27. A composition according to claim 21, wherein the hydrating agent in the outer layer has a concentration of from about 10% to about 30%, the hydrophilic polymer in the outer layer has a concentration of from about 25% to about 95%, and the hydrophobic polymer in the outer layer has a concentration of from about 0% to about 75%.

28. A composition according to claim 21, wherein the hydrating agent in the outer layer has a concentration of from about 15% to about 25%, the hydrophilic polymer in the outer layer has a concentration of from about 50% to about 85%, and the hydrophobic polymer in the inner layer has a concentration of from about 20% to about 100%.

29. A composition according to claim 21, wherein the hydrating agent has a concentration of about 20%, the hydrophilic polymer has a concentration of from about 75% to about 85%, and the outer layer comprises a hydrophobic polymer in a concentration of from about 0% to about 5%.

30. A coating liquid comprising:

a single phase solvent liquid adapted to dissolve or to disperse an ultrafine hydrating agent, comprising less than about 25% water by volume;

a hydrophilic polymer dissolved in the solvent liquid;

a hydrophobic polymer dissolved in the solvent liquid; and a hydrating agent in an amount of about 10% to about 50% as a percentage of the total weight of the hydrophilic polymer and hydrating agent, the hydrating agent being dissolved or an ultrafine dispersion having particle size less than about 10 microns;

the components of the coating liquid being mutually compatible and blended together, so that when the coating liquid is applied to a substrate and the solvent is removed, a homogeneous hydrophilic coating is formed that adheres to the substrate, becomes lubricious when wet, retains physiologically acceptable lubriciousness after contacting physiological media during a predetermined period of indwelling, is sufficiently smooth to avoid causing physiologically unacceptable trauma to tissue during insertion or removal, and has physiologically acceptable low cellular adhesiveness after contacting the tissue during a predetermined period of indwelling.

31. A coating liquid according to claim 30, wherein the concentration of hydrophilic polymer is from about 5% to about 10% w/v, the concentration of hydrophobic polymer is less than about 0.2% w/v, the concentration of water is less than about 10% by volume, and the hydrating agent is a salt.

32. A coating composition according to claim 30, wherein the solvent comprises a polar solvent and the hydrating agent is a dissolved salt.

33. A coating composition according to claim 30, wherein the solvent is selected from the group consisting of ketones, esters, toluene, lactones, dimethylformamide, halogenated solvents, tetrahydrofuran, dioxane, amines, glycol butyl ether, alkyl acetates, acetonitrile, butyrolactone, ethyl acetate, acetone, chloroform, methylethylketone, methylene chloride, ethylene chloride, methanol, ethanol, propanol, and mixtures thereof.

34. A coating composition according to claim 30, wherein the hydrophilic polymer comprises polyvinylpyrrolidone, the hydrating agent is an inorganic salt, and the solvent blend comprises a solvent selected from the group consisting of, by volume, about 11% to about 20% butyrolactone, about 50% to about 80% aliphatic alcohol, about 18% to about 30% acetone, up to about 25% ethylene glycol or propylene glycol, up to about 20% N-methylpyrrolidone, up to about 20% dimethylsulfoxide, up to about 15% glycerol, up to about 15% water, and combinations thereof.

35. A kit for coating a substrate comprising:

a single phase solvent adapted to dissolve or to disperse a hydrating agent, comprising an organic solvent and water in an amount up to about 25% by volume;

a hydrophilic polymer dissolved in the solvent;

a hydrating agent in an amount of about 10% to about 50% as a percentage of the total weight of the hydrophilic polymer and hydrating agent, in a form selected from the group consisting of hydrating agent dissolved in the solvent liquid, and hydrating agent dispersed in the solvent liquid as an ultrafine dispersion having particle size less than about 10 microns; and a hydrophobic polymer dissolved in an organic solvent; the components of the kit being mutually compatible when blended together, and capable of forming a homogeneous hydrophilic coating that adheres to the substrate, becomes lubricious when wet, is sufficiently smooth to avoid causing physiologically unacceptable trauma to tissue during insertion or removal, retains physiologically acceptable lubriciousness after prolonged contact with physiological media, and has physiologically acceptable low cellular adhesiveness after prolonged contact with tissue.

36. A coating kit according to claim 35, wherein the hydrophobic polymer is in a first coating liquid and the hydrophilic polymer and hydrating agent are in a second coating liquid.

37. A method of coating a substrate comprising:

providing a hydrophilic polymer dissolved in a solvent, the hydrophilic polymer solvent adapted to dissolve or to disperse a hydrating agent, and comprising less than about 25% water by volume;

adding to the hydrophilic polymer solvent a hydrating agent as an ultrafine dispersion having particle size less than about 10 microns, the method of adding being selected from (a) dissolving the hydrating agent in a hydrating agent solvent to produce a hydrating agent solution, then adding the hydrating agent solution streamwise into the hydrophilic polymer solution to produce an ultrafine dispersion of hydrating agent particles having particle size less than about 10 microns, and (b) without regard to order, adding an acid to the polymer solution, and adding a base to the polymer solution, so that the acid and base neutralize each other and form an ultrafine dispersed precipitate of hydrating agent;

coating the substrate with the hydrophilic polymer and hydrating agent in the hydrophilic polymer solvent; and forming a hydrophilic coating that adheres to the substrate, becomes lubricious when wet, retains physiologically acceptable lubriciousness after contacting physiological media during a predetermined period of indwelling, is sufficiently smooth to avoid causing physiologically unacceptable trauma to tissue during insertion or removal, and has physiologically acceptable low cellular adhesiveness after contacting the tissue during a predetermined period of indwelling.

* * * * *